United States Patent [19]

Sippel et al.

[11] Patent Number: 5,731,178
[45] Date of Patent: Mar. 24, 1998

[54] ATTACHMENT-ELEMENTS FOR STIMULATION OF EUKARYOTIC EXPRESSION SYSTEMS

[75] Inventors: Albrecht E. Sippel, Heidelberg; Aribert Stief, Müllheim, both of Germany

[73] Assignee: Behringwerke Aktiengesellschaft, Marburg, Germany

[21] Appl. No.: 451,308

[22] Filed: May 26, 1995

Related U.S. Application Data

[63] Continuation of Ser. No. 294,618, Aug. 23, 1994, abandoned, which is a continuation of Ser. No. 134,867, Oct. 12, 1993, abandoned, which is a continuation of Ser. No. 866,256, Apr. 10, 1992, abandoned, which is a continuation of Ser. No. 496,925, Mar. 21, 1990, abandoned.

[51] Int. Cl.$^6$ .............. C12N 15/11; C12N 15/67; C12N 15/85; C12P 21/02
[52] U.S. Cl. .................. 435/172.3; 435/69.1; 536/23.1; 536/74.1
[58] Field of Search ................ 435/172.3, 69.1; 536/24.1, 23.1

[56] References Cited

PUBLICATIONS

Goldberg et al. (1983), Cell 34: 59–73, 1983.
Hiromi et al. (1985), Cell 43: 603–613 1985.
Strätling et al., Biochem. 25 : 495–502 (1986).
Leutz et al., EMBO J. 3 : 3491–3499 (1984).
Mirkovich et al., Cell 39 : 223–232 (1984).
Southern, J. Mol. Biol. 98 : 503–517 (1975).
Rigby et al., J. Mol. Biol. 113 : 237–251 (1977).
Berezney and Coffey, Biochem. Biophys. Res. Comm. 60: 1410–1419 (1974).
Klehr et al (1991) Biochemistry 30, 1264–1270.
Mielke et al (1990) Biochemistry 29, 7475–7485.
McKnight et al (1992) Proced. Natl. Acad. Sci. 89, 6943–6947.
Gyurkovics et al (1990) EMBO J. 9, 2579–2585.
Kellum et al (1991) Cell 64, 941–950.
Gasser et al (1986) Cell 46, 521–530.
Cockerill et al (1986) Cell 44, 273–282.
Phi-Van and Strätling 1988 EMBO Jounal vol. 7, pp. 655–664.
Theisen et al. 1986 EMBO Journal vol. 5, 719–724.

*Primary Examiner*—Nancy Degen
*Attorney, Agent, or Firm*—Finnegan, Henderson, Farabow, Garrett & Dunner, L.L.P.

[57] ABSTRACT

The invention concerns methods to increase the expression of genes brought into eukaryotic cells or organisms. By flanking a transcription unit EPC made up by e.g. an enhancer (E), promoter (P), and the (structural) gene of interest (C) with attachment-elements (A) the expression of said (structural) gene of interest is stimulated when integrated into the genome of eucaryotic cells and is independent of its chromosomal position. Thus a construct AEPCA is advantageous because it constitutes an independant regulatory unit.

4 Claims, 4 Drawing Sheets

ATTACHMENT-ELEMENTS FOR STIMULATION OF EUKARYOTIC EXPRESSION SYSTEMS

This application is a continuation of application Ser. No. 08/294,618, filed Aug. 23, 1994, now abandoned, which is a continuation of application Ser. No. 08/134,867, filed Oct. 12, 1993, now abandoned, which is a continuation of application Ser. No. 07/866,256, filed Apr. 10, 1992, now abandoned, which is a continuation of application Ser. No. 07/496,925, filed Mar. 21, 1990, now abandoned.

The invention concerns methods to increase the expression of genes brought into eukaryotic cells or organisms. By flanking a transcription unit EPC made up by e.g. an enhancer (E), promoter (P), and the (structural) gene of interest (C) with attachment-elements (A) the expression of said (structural) gene of interest is stimulated when integrated into the genome of eukaryotic cells and is independent of its chromosomal position. Thus a construct AEPCA is advantageous because it constitutes an independant regulatory unit.

Transfecting eukaryotic cells with DNA constructs for expression of genes of interest results in a stable expression by integration of the DNA constructs into the host cell genome. However, the integration events happen in a random manner. This means that the gene of interest respective the transcriptional unit EPC will be integrated randomly at any locations of the host cell genome. The amount of product expressed from said EPC in single cell clones is generally not predictable. It depends from the gene doses and the chromosomal position of the integration event. The gene doses alone, that is the copy number of the integrated transcriptional units, does not correlate with the amount of gene product expressed.

There was thus a long felt need for reliable processes realizing a high expression from a gene of interest integrated into a eukaryotic host in a form which is not dependent on the position of said gene within the host genome. As a result of these methods there should then be a direct correlation between the level of expression and the gene-doses of the inserted gene of interest.

It was found that genomic DNA regions which are attached to the nuclear matrix or nuclear scaffold (L. Phi Van and W. H. Strätling, (1988), EMBO J. 7, 655–664) and which at the same time are borders of an active chromatin domain of elevated general DNase sensitivity (as described in: Weintraub and Groudine (1976) Science 193, 848–856) greatly stimulate expression of a gene of interest within a transcription unit EPC. This stimulation is seen when these elements (A-elements for attachment-elements) are put into a flanking array AEPCA. The stimulating effect is in this configuration also independent of the site of stable integration into the genome.

A-elements are described e.g. for the chromatin domain of the chicken lysozyme gene as "matrix attachment regions (MAR)" by Phi Van and Strätling (a.a.O.). They are isolated by a binding method described by Phi Van and Strätling (a.a.O.) and P. N. Cockerill and W. T. Garrard (1986), Cell 44, 273–282), wherein A-elements are bound to the nuclear matrix and wherein the nuclear matrix is isolated according to these publications which represent modifications of the methods published by R. Berezney and D. Coffey ((1974), Biochem. Biophys. Res. Comm. 60, 1410–1419). Stimulation takes place in cis-mode for the inserted gene of interest C within the AEPCA array. Preferred as sources for A-elements are small, highly expressed transcription units like the chromatin domain of the chicken lysozyme gene.

The invention therefore concerns the method of use of attachment-elements (A) for stimulation of eukaryotic expressions systems by flanking a transcription unit EPC with A-elements resulting in the configuration AEPCA. In preferred embodiments of the invention the A-elements are taken from small, highly expressed transcription units, in still more preferred embodiments they are taken from the chromatin domain of the chicken lysozyme gene (5' or 3' A-element).

In a most preferred embodiment the A-element comprise the fragment B1-XI (nucleotides −11.7 kb through −8.7 kb) or the fragment E6-E7 (nucleotides +5.3 kb through +9.0 kb) of the chicken lysozyme locus as described by Phi-Van and Strätling (a.a.o.).

Furthermore, the invention is illustrated but not limited by the examples.

EXAMPLES

1. Synthesis of Gene Configurations PC, EPC, APCA and AEPCA

In this and the following examples the chicken lysozyme promoter (P), the lysozyme enhancer (E), a reporter gene (C) encoding chloramphenicol acetyltransferase (CAT), and the 5' A-element of the chicken lysozyme gene were used. FIG. 1 illustrates the construction of AEPCA and the relative position of the enhancer (nucleotides −6331 to −5772), the promoter (nucleotides −579 to +15), and the 5' A-element (B1-X1 fragment in Phi Wang and Strätling (a.a.o.) spanning the region −11700 to −8700). The 5' A-element was prepared as described in Phi Van and Strätling. Specifically, HD11 cells were prepared as described previously. Leutz et al., EMBO J. 3:3491–3499 (1984). $1 \times 10^7$ cells were washed once in phosphate buffered saline, detached by treatment with trypsin, and washed four times in isolation buffer comprising 5 mM Tris-HCl, 20 mM KCl, 0.125 mM spermidine, 0.05 mM spermine, 0.1% digitonin (Fluka), 0.5 mM Na-EDTA, 0.5% Trasylol, 0.1 mM PMSF, pH 7.5. Following suspension in isolation buffer without EDTA, extraction of nuclei was performed as described by Mirkovich et al., Cell 39:223–232 (1984), except that the concentration of lithium diiodosaicylate was reduced to 12.5 mM and the pH of the extraction buffer was carefully adjusted at pH 7.4. Nuclear halos were digested with 1000 U BamHI and 1300 U XbaI for 2 hours at 37° C., and DNA was purified from solubilized (S) and insoluble (P) fractions. Naked DNA from intact nuclei (T) was transferred according to Southern (J. Mol. Biol. 98:503–517 (1975)) to nitrocellulose filters and hybridized with $^{32}$P-labeled, nick-translated, Rigby et al., J. Mol. Biol. 113:237–251 (1977), DNA probes as described previously (Strätling et al., Biochemistry 25:495–502 (986)). Construction of plasmids containing PC or EPC is described by M. Theisen et al. ((1986) EMBO J. 5, 719–724) with plasmids pLYSCAT 2000 and pLYSCAT 2100 respectively. Plasmids containing the "mini-domains" APCA and AEPCA were constructed by blunt-end ligation of the lysozyme-gene 5' A-element into the XbaI and/or the BamHI site of plasmids containing PC or EPC. The A-element was inserted in sense as well as in anti-sense orientation. The reporter gene C (CAT) was isolated without its promoter from plasmid pCAT3U (E. B öhnlein et al. (1985) Nucleic Acids Res. 13, 4789–4809).

2. Effect of A-Elements on the Activity of Stably Integrated Reporter Genes

Plasmids containing the foregoing constructions PC, EPC, APCA and AEPCA were cotransfected in separate experiments with plasmids carrying a neomycin resistance gene (D. Canaami and P. Berg (1982) Proc. Acad. Natl. Sci. 79, 5166–5170) into chicken HD 11/HBCI-promacrophage cells, in which the endogenous lysozyme gene as well as the lysozyme enhancer are active.

Promacrophage cell lines that were clonaly derived and resistant to neomycin were isolated. Each of these clones represents an individual integration event. FIGS. 2a, 2b, 2c and 2d summarize the result of an analysis of 58 cell lines, in which the transfected DNA constructs were correctly integrated into the genome of the host cell. The relative CAT activity has been plotted versus the copy number of the integrated plasmid DNAs (tandem configuration), as determined by quantitative Southern blots. The panels demonstrate the clonal distribution of genomic insertion events with PC-, EPC-, APCA- and AEPCA DNA (FIGS. 2a, d). The comparison of CAT activities produced by the two constructs that lacked A-elements clearly demonstrates that the enhancer has an average stimulatory effect when it is in a genomic location. The CAT activities of individual enhancer-activated cell lines, however, differed considerably (FIG. 2b). This variability exemplifies the commonly observed copy-number independence that results from the genomic position effect. Experiments utilizing transient expression, that is without integration of the constructions above into the genome, did not show a stimulatory effect of the A-elements within the same constructs (FIG. 3).

The presence of A-elements at both ends of the integrated DNA dramatically affected the activity of the reporter gene in two ways. First, comparisons of the CAT activity of PC-containing cells with that of APCA-containing cells (FIGS. 2a, 2c) and of the CAT activity of EPC-containing cells with that of AEPCA-containing cells (FIGS. 2b, 2d), show that there was significant A-element-dependent stimulation for the reporter-gene activity. Second, consistently high-level CAT activity that was dependent on the copy number was obtained in AEPCA-containing cells (FIG. 2d), in which the inserted DNA elements resemble the arrangement of the endogenous domain of the lysozyme gene. A-elements appear to buffer the inserted "mini-domain" from the influence of nearby genomic regions. Both of the A-element activities—the stimulatory activity as well as the activity that produced independence of the integration site—were found, irrespective of the orientation of the upstream A-element (FIG. 2d and FIG. 4).

DNA transfection was as described by Theisen et al. (a.a.O.). Plasmid (2 μg) containing the neomycin-resistance gene linked to the long terminal repeat promoter of the murine-leukemia-virus and the poly (A) signal of the thymidine kinase (tk) gene of the herpes simplex virus (pMPlneo), and 48 μg of the different CAT plasmid constructs were cotransfected into 2×10⁶ promacro-phages. 72 h later, cells were harvested, diluted (1:3) with medium containing 500 μg ml⁻¹ G418 antibiotic. After 4 weeks, G418-resistant clones were isolated. Integration of transfected DNA was analysed by Southern blotting of 10 μg genomic DNA (BamH1 digestion of PC- and EPC-containing cell DNA, ClaI digestion of APCA- and AEPCA-containing cell DNA) and hybridization with the probe shown in FIG. 1. On average, 50% of clones showed correct integration; clones with incorrectly integrated DNA were discarded. Copy numbers of integrated DNA were determined by quantitative Southern blotting. DNA of clones with correctly integrated DNA was digested with EcoRI and hybridized with the probe shown in FIG. 1. Signal intensities were compared with standards derived from dilution series of plasmid DNA. CAT activity was determined as described by Theisen et al. (a.a.O.). 1 unit of relative CAT activity represents the conversion of 1% chloramphenicol by incubation with 300 μg extract protein for 1 h at 37° C. (86.6 pmol acetylated chloroamphenicol per mg of protein per hour).

By quantitative S1-nuclease mapping of the reporter gene transcripts in three AEPCA-containing and three EPC-containing cell lines (see arrows in FIG. 2b and FIG. 2d) it was furthermore possible to demonstrate that the level of transcipts parallels the activity of the reporter gene (see FIGS. 4). The transcriptional stimulation by the A-elements add to the stimulatory activity of the enhancer (FIG. 2a, 2b, 2c and 2d), yet A-elements and the enhancer stimulate in a functionally distinguishable manner. A-elements do not stimulate in transient transfection systems (see FIG. 3) when not integrated in a stable way into the genome. They appear to buffer the position effect. Enhancers stimulate gene activity also in transient transfection systems and do not overcome the position effect.

3. Stimulation of Gene Expression in Heterologous Cell Systems by A-Elements

The chicken lysozyme 5' and 3' A-elements stimulate gene expression in heterologous cell systems (cells of different vertebrate species and of different cell-type specificity). FIG. 4 outlines an experiment in which A-element containing and not containing constructs were used for the stable transfection of mouse L-cells, a fibroblast cell line. The results also show that chicken A-element function is not dependent on the cooperation with a chicken enhancer. The lysozyme 5' A-element used drastically stimulates reporter gene constructs containing BK virus enhancer. When stably integrated into the genome without A-elements the viral enhancer shows low additional activity of EPC- over PC-constructs (FIG. 4). Since APCA constructs show only base level reporter gene activity we conclude that the presence of an enhancer is essential for full A-element function. The experiment outlined in FIG. 4 demonstrates that the chicken A-elements themselves have no own regulatory specificity but rather stimulate the expression from whatever functioning transcriptional unit plus enhancer is positioned in between the two of them.

Diagram of the genomic organization of the chicken lysozyme gene and of the construct containing an AEPCA "mini-domain".

In genomic location, the lysozyme domain (−12 kb to +9 kb) is flanked by 5' (dotted box) and 3' (hatched box) DNA attachment elements. The enhancer element (nucleotides −6,331 to −5,772), the promoter element (nucleotides −579 to +15) and the coding region with exons and introns (box with filled and open bars) are detailed. Arrowheads mark the positions of DNase-I-hypersensitive sites in the chromatin of various cell types. In the construct containing the AEPCA mini-domain (not to scale), the reporter gene CAT, which is linked to the lysozyme-gene promoter and enhancer, is flanked by two lysozyme-gene 5' A-elements (B1-X1 DNA fragment corresponding to nucleotides −11.7 to −8.7 kb). Restriction sites and the probe relevant for Southern blot analysis are indicated: ClaI (Cla), EcoRI (Eco), BamHI (Bam).

FIG. 2

Effect of A-elements on the activity of stably integrated reporter genes.

Each dot represents 1 of 58 stably transfected HD11/HBCI cell clones of two independent series of experiments (open and closed symbols). Copy number of correctly inserted DNA as determined by quantitative Southern blot analysis is plotted versus relative CAT activity.

2a, 11 clones with inserted PC-containing plasmid DNA;

2b, 19 clones of EPC-containing cells;

2c, 10 clones of APCA-containing cells;

2d, 18 clones of AEPCA-containing cells.

Figure 1:
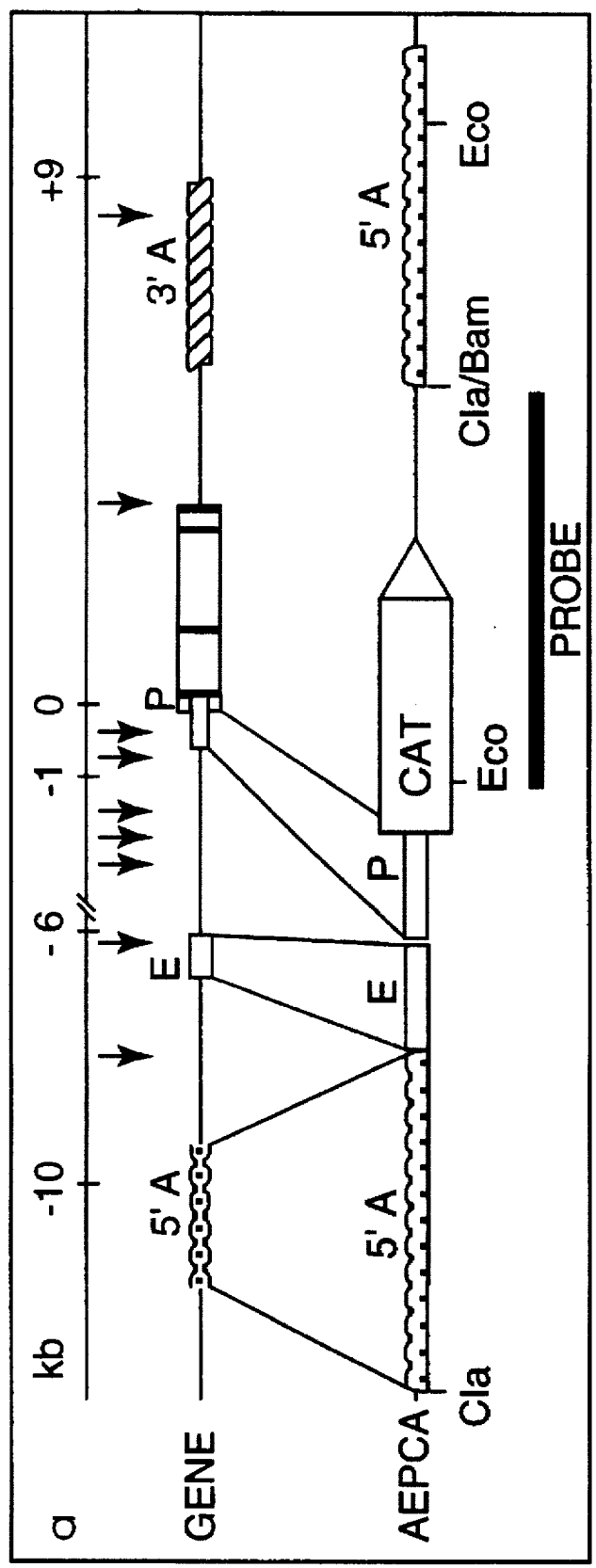
FIG. 1
Figures 2A, 2B, 2C, 2D:
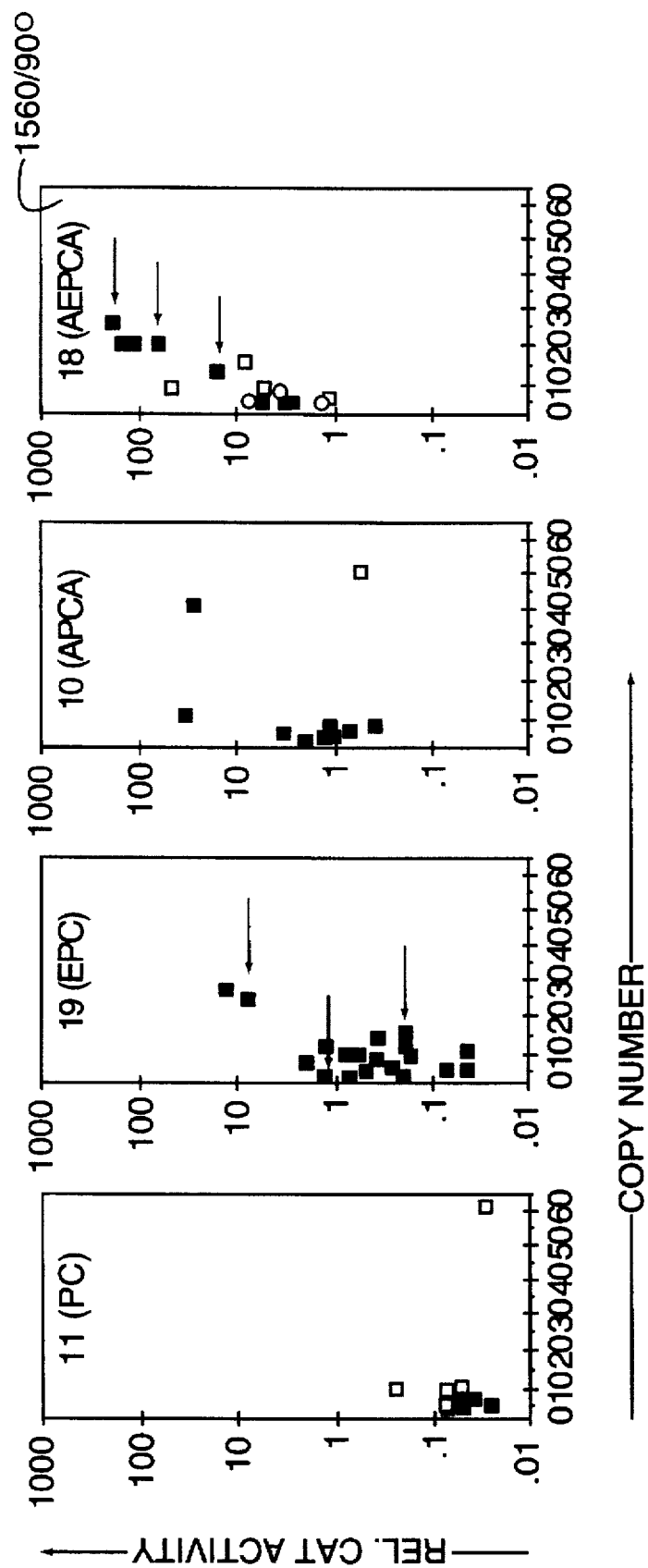
Figure 3:
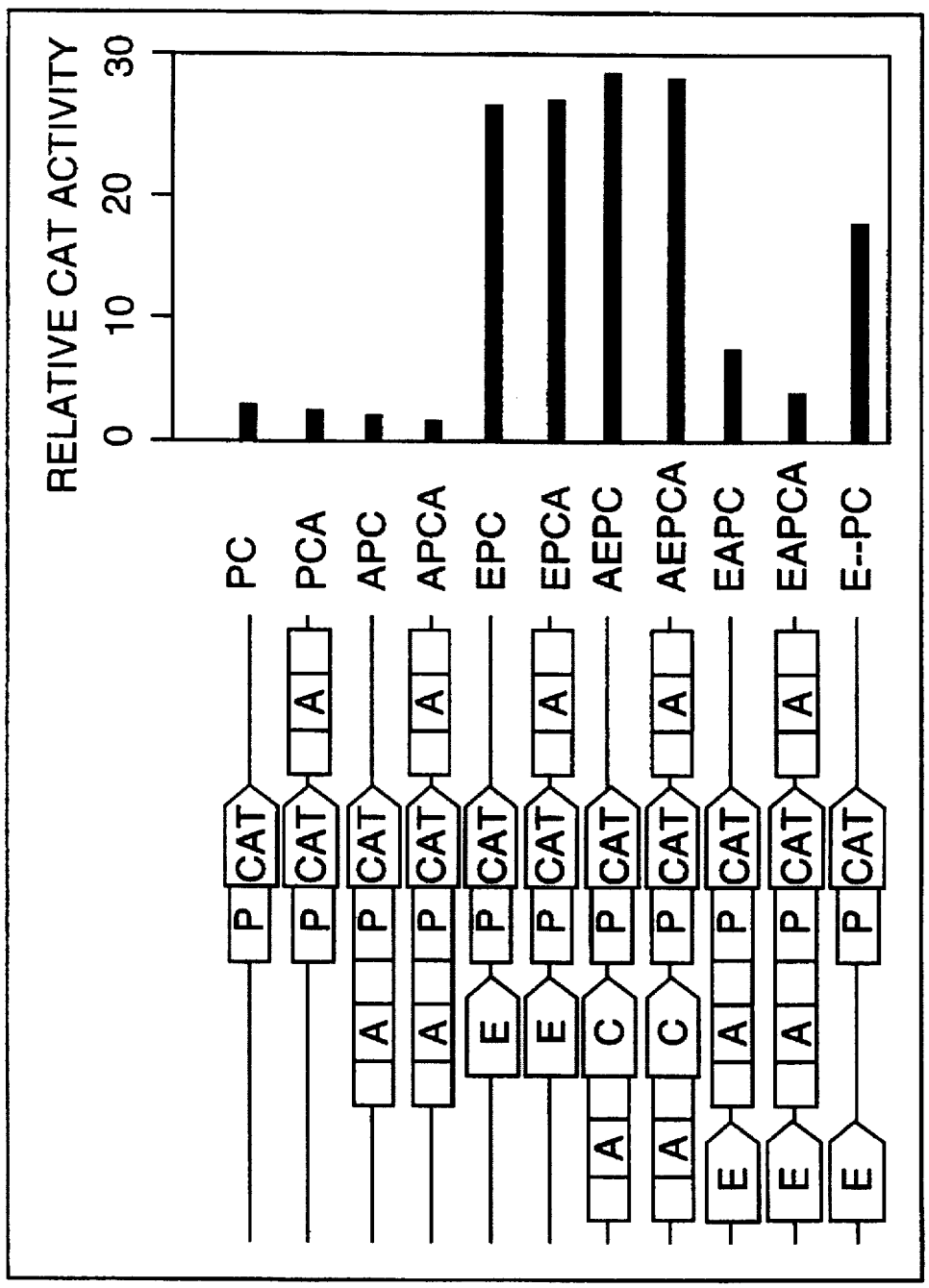
Figure 4:
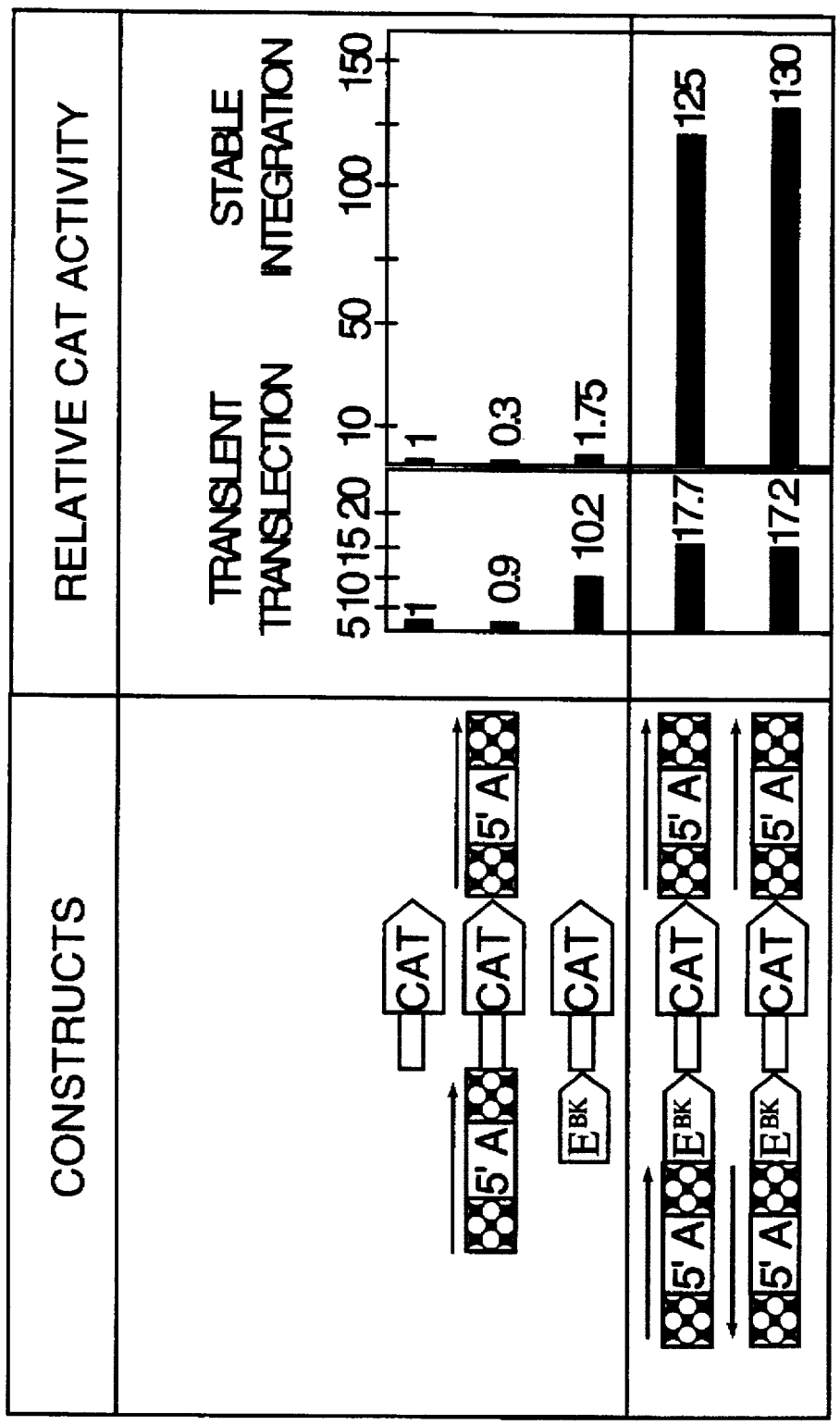

Control experiments demonstrated that A-elements in integrated constructs containing AEPCA retained the ability to attach to the nuclear matrix or scaffold obtained from lithium 3', 5'-diiodosalixylate-extracted nuclei. In AEPCA-containing cells, represented by circles, the upstream A-element is in sense orientation; those cells represented by squares have the A-element in the anti-sense orientation. Arrows mark cell clones used for further analysis. The AEPCA cell clone (represented by an open circle in the right upper corner of FIG. 2d) has the value of relative CAT activity 1560 and the copy number 90, as indicated.

FIG. 3

Relative CAT activity of different PC constructs with A-elements (A) and the chicken lysozyme enhancer (E) for transient expression.

CAT activity was measured 45 hours after transfection, relative CAT activity means the percentage of chloramphenicol acetylated by 10 μl of cell extract incubated for 1 h at 37° C. Values are averages of three independent transfection experiments each.

FIG. 4

Functional analysis of the chicken lysozyme 5' A-element in mouse L-cells.

The left panel shows the reporter gene constructs used for transient and stable transfection experiments in mouse Ltk⁻-cells. Open bars designate the lysozyme promoter, $E^{BK}$ depicts the BK-virus enhancer HaeIII fragment (Rosenthal et al. (1983) Science 222, 749–754), black and white checkered boxes show the 5' A-element of the chicken lysozyme gene. Arrows designate the orientation of the A-elements. For transient gene transfer $1.5 \times 10^6$ mouse L-cells were transfected by the calcium phosphat technique with 25 μg reporter gene plasmids. After 48 h CAT activity was determined and relative activities in respect to the activity of PC cells are plotted. Values are averages of three independent experiments. The result of stably transfected cell populations, each representing an average of a total of about 300 clonal integration events (as described in the legend to FIGS. 2a, 2b, 2c and 2d) are shown on the right panel.

We claim:

1. A recombinant DNA molecule comprising attachment elements 5' and 3' to a transcription unit forming an A-element containing transcription unit, wherein said transcription unit comprises an enhancer and a promoter, and further wherein said promoter is operably linked to a heterologous structural gene.

2. The recombinant DNA molecule as claimed in claim 1, wherein said attachment elements are obtainable from the chromatin domain of the chicken lysozyme gene.

3. The recombinant DNA molecule as claimed in claim 1, wherein said attachment elements are selected from the group consisting of nucleotides −11.7 through −8.7 kb and nucleotides +5.3 kb through +9.0 kb of the chicken lysozyme locus.

4. A method of increasing expression of a transcription unit in an eukaryotic host which comprises:

integrating into the genome of the eukaryotic host a DNA molecule containing a transcription unit and attachment elements (A) at the 3' and 5' ends of said transcription unit, such that said transcription unit is expressed in said eukaryotic host, wherein said transcription unit comprises an enhancer (E), a promoter (P), and a structural gene (C) that is heterologous to said eukaryotic host, resulting in a gene array of AEPCA.

* * * * *